United States Patent [19]

Nishimura et al.

[11] Patent Number: 5,324,841
[45] Date of Patent: Jun. 28, 1994

[54] METHOD OF CHLORINATING SIDE CHAIN OF 2-CHLORO-METHYLPYRIDINE

[75] Inventors: Yasunobu Nishimura, Kawagoe; Yukikazu Itou, Ube; Asao Morino, Ube; Katuya Nishihara, Ube; Shinya Kawamura, Ube, all of Japan

[73] Assignee: Central Glass Company, Ube, Japan

[21] Appl. No.: 21,434

[22] Filed: Feb. 24, 1993

[30] Foreign Application Priority Data

Feb. 26, 1992 [JP] Japan ................................. 4-039808

[51] Int. Cl.$^5$ .................. C07D 213/26; C07D 213/61
[52] U.S. Cl. ...................................... 546/345; 546/346
[58] Field of Search ............................... 546/345, 346

[56] References Cited

U.S. PATENT DOCUMENTS

| 4,612,377 | 9/1986 | Osborne | 546/345 |
| 4,778,896 | 10/1988 | Gallenkamp | 546/345 |
| 5,198,549 | 3/1993 | Günther | 546/345 |

FOREIGN PATENT DOCUMENTS 0260485 3/1988 European Pat. Off.
0485109 11/1991 European Pat. Off.
1204231 11/1965 Fed. Rep. of Germany.
49-127977 12/1974 Japan.

OTHER PUBLICATIONS

CA 116:83696u, Guenther et al, (DE:4016175), Nov. 1991.
Chem. Abstracts, vol. 84, 1976, Abs. No. 121665p, T. Hattori et al.
Angewandte Chemie, vol. 75, 1963, (Weinheim), pp. 235-240.

*Primary Examiner*—C. Warren Ivy
*Assistant Examiner*—D. Margaret M. Mach
*Attorney, Agent, or Firm*—Keck, Marin & Cate

[57] ABSTRACT

The invention relates to a method of chlorinating a side chain methyl group of 2-chloro-methylpyridine. The method comprising the steps of:(a) reacting said 2-chloro-methylpyridine with chlorine radical so that hydrogen chloride and/or hydrochloride of 2-chloro-methylpyridine are formed; and (b) neutralizing said hydrogen chloride and/or said hydrochloride of said 2-chloro-methyl-pyridine with a basic solution so as to chlorinating a side chain methyl group of said 2-chloro-methylpyridine.

10 Claims, No Drawings

METHOD OF CHLORINATING SIDE CHAIN OF 2-CHLORO-METHYLPYRIDINE

BACKGROUND OF THE INVENTION

The present invention relates to a method of chlorinating a side chain methyl group of 2-chloro-methylpyridine so as to produce 2-chloro-monochloromethylpyridine, 2-chloro-dichloromethylpyridine and/or 2-chloro-trichloromethylpyridine. These products are useful as raw materials of medicines such as anti-peptic ulcer and of insecticides.

In chlorination of a side chain methyl group of methylpyridine, hydrogen chloride produced by chlorination reacts with methylpyridine because nitrogen atom of pyridine nucleus functions as a base. With this, hydrochloride of methylpyridine is produced. As a side chain methyl group of methylpyridine is chlorinated to a higher order, electron attractivity of a side chain methyl group increases. With this, basicity of nitrogen atom decreases. Therefore, as compared with chlorinated methylpyridine, methylpyridine predominantly reacts with hydrogen chloride so as to produce hydrochloride of methylpyridine. This hydrochloride precipitates in the form of solid, and is very low in reactivity with chlorine. Therefore, it becomes difficult to successively chlorinate methylpyridine.

There are some proposals to prevent the formation of hydrochloride of methylpyridine. For example, as is disclosed in Angew. Chem. Internat. Edit., 144, 2 (1963) and German Patent 3,630,046, there is provided a method of chlorinating a side chain methyl group of methylpyridine in the presence of an inactive solvent and a hydrogen chloride acceptor such as sodium carbonate. JP-A-49-127977 discloses a method of chlorinating a side chain methyl group of methylpyridine in the presence of an inactive solvent, a hydrogen chloride acceptor and water.

However, if the above-mentioned methods are applied to chlorination of 2-chloro-methylpyridine which is represented by the following formula (1), chlorination will be stopped in the middle of the reaction due to the presence of water as an additive and/or water which is formed by neutralization of hydrogen chloride and a hydrogen chloride acceptor.

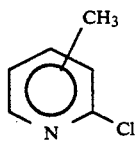

(1)

In particular, in the case that water is added as an additive or as the reaction system is enlarged in size, chlorination is substantially inhibited. It is believed that a hydrogen chloride acceptor is dissolved in water and directly reacts with chlorine so as to prevent the formation of chlorine radical and thus to stop chlorination.

In the above conventional methods, a hydrogen chloride acceptor such as sodium carbonate in the form of solid is added. Therefore, the reaction liquid takes the form of slurry. Thus, it is necessary to add an inactive solvent such as carbon tetrachloride for adjusting the concentration of the slurry. However, the usage of a halogen-containing hydrocarbon such as carbon tetrachloride will be limited in the future from an environmental aspect and furthermore is not economical.

SUMMARY OF THE INVENTION

It is therefore an object of the present invention to provide an improved method of chlorinating a side chain methyl group of 2-chloro-methylpyridine.

According to the present invention, there is provided a method of chlorinating a side chain methyl group of 2-chloro-methylpyridine which is represented by the above formula (1). the method comprising the steps of:

(a) reacting said 2-chloro-methylpyridine with chlorine radical so that hydrogen chloride and/or hydrochloride of 2-chloro-methylpyridine are formed; and (b) neutralizing said hydrogen chloride and/or said hydrochloride of said 2-chloro-methylpyridine with a basic solution so as to chlorinate a side chain methyl group of said 2-chloro-methylpyridine.

According to the present invention, chlorination proceeds smoothly even in the presence of water, thereby producing 2-chloro-monochloromethylpyridine, 2-chloro-dichloromethylpyridine and/or 2-chloro-trichloromethylpyridine with a high yield and a high selectivity.

DESCRIPTION OF THE PREFERRED EMBODIMENTS

The present invention can be applied to chlorinate 2-chloro-methylpyridine, i.e. 2-chloro-3-methylpyridine, 2-chloro-4-methylpyridine, 2-chloro-5-methylpyridine and 2 -chloro-6-methylpyridine.

In chlorination according to the present invention, chlorine radical is formed. In this radical reaction, chlorine gas is bubbled into the reaction liquid in the presence of a hydrogen chloride acceptor. For example, chlorine radical is formed by the addition of a radical initiator. Examples of radical initiators are aliphatic azo-compounds such as 2,2'-azobisisobutyro-nitrile (AIBN) and peroxides such as benzoylperoxide (BPO). The amount of radical initiator is not particularly limited as long as the formation of chlorine radical becomes sufficient. However, it is preferably from 0.01 to 10% of the substrate, and more preferably from 0.1 to 5% of the substrate. A radical initiator can be added continuously or intermittently to the reaction liquid before chlorination and/or during chlorination. It is optional to form chlorine radical by the application of ultraviolet rays.

In the present invention, a basic solution is added to the reaction liquid so as to neutralize hydrogen chloride and/or hydrochloride of 2-chloro-methylpyridine. With this, hydrochloride of 2-chloro-methylpyridine is turned into 2-chloro-methylpyridine. By the addition of a basic solution, the reaction liquid is separated into two phases, i.e. water phase and 2-chloro-methylpyridine phase. However, this phenomenon is not an obstacle to chlorination.

It is necessary to control pH value of the reaction liquid by the addition of a basic solution so as to fall within a range from 0.5 to 3, and preferably from 0.8 to 2.5. If pH value becomes below 0.5, a large amount of hydrochloride of 2-chloro-methylpyridine is produced. As is mentioned hereinabove, this hydrochloride does not react with chlorine, thereby stopping chlorination. If pH value becomes over 3, elementary chlorine in the reaction liquid is ionized. This inhibits the formation of chlorine radical, thereby stopping chlorination.

In the present invention, a useful basic solution for neutralization of hydrogen chloride and/or hydrochloride of 2-chloro-methylpyridine is a solution of carbonate of alkali metal or alkali earth metal, a solution of bicarbonate of alkali metal or alkali earth metal, or a solution of hydroxide of alkali metal or alkali earth metal. The concentration of a basic solution is not particularly limited int he present invention. Either of saturated and unsaturated basic solutions can be used in the present invention. Thus, the usage of a base which has a high saturation solubility in water is effective for decreasing the amount of basic solution to be added to the reaction liquid. After neutralization, an alkali metal chloride or an alkali earth metal salt may precipitates. However, tis precipitation is not an obstacle to chlorination. If desired, the precipitation can be prevented by adjusting the concentration of a basic solution or by adding a suitable amount of water to the reaction liquid.

The application manner of a basic solution is not limited to a specific one in the present invention. For example, a basic solution can be continuously or intermittently dropped int the reaction liquid.

In the present invention, it is not necessary to add an organic solvent. However, if desired, a solvent which is inactive in chlorination, such as o-dichlorobenzene or a halogenated hydrocarbon such as carbon tetrachloride can be used.

The reaction temperature in chlorination is preferably from 50° C. to a reflux temperature, and more preferably from 60° to 90° C.

As is mentioned hereinabove, according to the present invention, 2-chloro-methylpyridine is chlorinated. However, it is needless to say that the present invention can be applied to chlorination of other methylpyridines which are weak in complexation capacity with chlorine.

EXAMPLE 1

In this example, 2-chloro-4-methylpyridine was chlorinated in accordance with the following steps.

First, 100 g (784.3 mmol) of 2-chloro-4-methylpyridine was mixed with 100.0 g of water in a reaction vessel. The mixture was stirred and liquid temperature was raised up to 65° C. After that, 1.0 g of AIBN was added to the mixture. In 10 min after the addition of AIBN, chlorine gas was bubbled into the mixture at a rate of 9.6 g/hr, and liquid temperature was maintained at a temperature ranging from 65° to 67° C. during the bubbling. In 15 min after the initiation of bubbling, induction period of chlorination appeared. In 30 min after the initiation of bubbling, a continuous dropping of 25% potassium carbonate solution was began with using a quantitative pump at a rate of 32.2 g/hr. During the dropping, pH value of the reaction liquid was maintained within a range from 1 to 2. In every 1 hr after the initiation of bubbling of chlorine gas, 1.0 g of AIBN was added to the reaction liquid. Chlorination was continued for 6.5 hr. After chlorination, the reaction liquid was cooled down to room temperature. Then, 87.5 g of 25% potassium carbonate solution was dropped into the reaction liquid so as to make the same basic. Then, the reaction product was extracted from the reaction liquid with ethyl acetate. The extract was dried with anhydrous magnesium sulfate. Then, ethyl acetate was distilled off under reduced pressure. With this, oil having pale yellow color was recovered as the reaction product. By the analysis with a gas chromatograph, it was found that the reaction product contained 19.2% of 2-chloro-4-methylpyridine which is a non-chlorinated raw material, 62.5% of 2-chloro-4-monochloromethylpyridine, 16.5% of 2-chloro-4-dichloromethylpyridine and 0.4% of 2-chloro-4-trichloromethylpyridine.

EXAMPLE 2

In this example, 2-chloro-6-methylpyridine was chlorinated in accordance with the following steps.

First, 10.0 g (78.4 mmol) of 2-chloro-6-methylpyridine was mixed with 10.0 g of water in a reaction vessel. The mixture was stirred and liquid temperature was raised up to 65° C. After that, 0.1 g of AIBN was added to the mixture. In 10 min after the addition of AIBN, chlorine gas was bubbled into the mixture at a rate of 1.3 g/hr, and liquid temperature was maintained at a temperature ranging from 67° to 70° C. during the bubbling. In 10 min after the initiation of bubbling, induction period of chlorination appeared. In 45 min after the initiation of bubbling, 2.16 g (3.91 mmol) of 25% potassium carbonate solution was dropped into the reaction liquid. After that, 2.16 g of 25% potassium carbonate solution was intermittently dropped into the reaction liquid at intervals of 30 min. In 3 hr after the initiation of bubbling of chlorine gas, 0.1 g of AIBN was added to the reaction liquid. Chlorination was continued for 5 hr. After chlorination, the reaction liquid was cooled down to room temperature. Then, 6.48 g of 25% potassium carbonate solution was dropped into the reaction liquid so as to make the same basic. Then, the reaction product was extracted from the reaction liquid with ethyl acetate. The extract was dried by anhydrous magnesium sulfate. Then, ethyl acetate was distilled off under reduced pressure. With this, oil having pale yellow color was recovered as the reaction product. By the analysis with a gas chromatograph, it was found that the reaction product contained 20.0% of 2-chloro-6-methylpyridine which is a non-chlorinated raw material, 60.6% of 2-chloro-6-monochloromethylpyridine, 16.0% of 2-chloro-6-dichloromethylpyridine and 0.3% of 2-chloro-6-trichloromethylpyridine.

EXAMPLES 3-5

In Examples 3-5, 2-chloro-3-methylpyridine, 2-chloro-4-methylpyridine and 2-chloro-5-methylpyridine were respectively chlorinated in accordance with the steps of Example 2.

In Example 3, it was found that the reaction product contained 22.1% of 2-chloro-3-methylpyridine which is a non-chlorinated raw material, 65.6% of 2-chloro-3-monochloromethylpyridine, 10.8% of 2-chloro-3 -dichloromethylpyridine and 0.5% of 2-chloro-3-trichloromethylpyridine.

In Example 4, it was found that the reaction product contained 21.1% of 2-chloro-4-methylpyridine which is a non-chlorinated raw material, 61.3% of 2-chloro-4-monochloromethylpyridine, 16.6% of 2-chloro-4-dichloromethylpyridine and 0.1% of 2-chloro 4-trichloromethylpyridine.

In Example 5, it was found that the reaction product contained 11.5% of 2-chloro-5-methylpyridine which is a non-chlorinated raw material, 68.0% of 2-chloro-5-monochloromethylpyridine, 19.2% of 2-chloro-5-dichloromethylpyridine and 0.4% of 2-chloro-5-trichloromethylpyridine.

What is claimed is:

1. A method of chlorinating a side chain methyl group of 2-chloro-methylpyridine which is represented by the following formula (1),

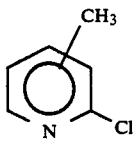 (1)

the method comprising the steps of:
(a) forming a reaction liquid comprising a 2-chloro-methylpyridine and a chlorine radical so that hydrochloride of 2-chloro-methylpyridine and optionally hydrogen chloride are formed; and
(b) controlling the pH of the reaction liquid of step a) by the addition of a basic solution so that the pH of the reaction liquid falls within a range of 0.5 to 3.0 so as to chlorinate a side chain methyl group of the 2-chloro-methylpyridine.

2. A method according to claim 1, wherein pH value of reaction liquid is controlled by said neutralization so as to fall within a range from 0.8 to 2.5.

3. A method according to claim 1, wherein said chlorine radical is formed by the addition of a radical initiator.

4. A method according to claim 3, wherein said radical initiator is one of an aliphatic azo-compound, or a peroxide.

5. A method according to claim 1, wherein said basic solution is a solution of an alkali metal carbonate or an alkali earth metal carbonate.

6.1 A method according to claim 1, wherein said basic solution is a solution of an alkali metal bicarbonate or an alkali earth metal bicarbonate.

7. A method according to claim 1, wherein said basic solution is a solution of an alkali metal hydroxide or an alkali earth metal hydroxide.

8. A method according to claim 1, wherein said basic solution is added continuously or intermittently to said reaction liquid so as to control pH value of said reaction liquid to fall within a range from 0.5 to 3.

9. A method according to claim 1, wherein temperature of said reaction liquid is controlled to fall within a range from 50°0 C. to a reflux temperature.

10. A method according to claim 9, wherein temperature of said reaction liquid is controlled to fall within a range from 60° to 90° C.

* * * * *